US008253076B2

(12) United States Patent
Andel et al.

(10) Patent No.: US 8,253,076 B2
(45) Date of Patent: Aug. 28, 2012

(54) RESPIRATORY SYSTEM HEATER UNIT

(75) Inventors: David F. Andel, Lawrenceville, GA (US); Keith J. Bradley, Atlanta, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1107 days.

(21) Appl. No.: 11/927,038

(22) Filed: Oct. 29, 2007

(65) Prior Publication Data

US 2009/0107981 A1 Apr. 30, 2009

(51) Int. Cl.
*H05B 3/68* (2006.01)
*F28F 1/30* (2006.01)
(52) U.S. Cl. .................. 219/443.1; 165/182
(58) Field of Classification Search .... 219/443.1–464.1, 219/538–541; 165/181, 182, 185; 392/322, 392/324, 386
See application file for complete search history.

(56) References Cited

U.S. PATENT DOCUMENTS

| 2,526,890 | A | * | 10/1950 | Mendel | 126/39 C |
| 2,715,173 | A | * | 8/1955 | Farquharson | 219/450.1 |
| 3,374,452 | A | * | 3/1968 | Judd | 336/60 |
| 3,659,604 | A | * | 5/1972 | Melville et al. | 128/203.27 |
| 3,896,481 | A | | 7/1975 | Calabro | |
| 3,961,666 | A | | 6/1976 | Suzuki et al. | |
| 4,051,205 | A | | 9/1977 | Grant | |
| 4,124,794 | A | | 11/1978 | Eder | |
| 4,191,875 | A | * | 3/1980 | Cunningham | 219/623 |
| 4,241,718 | A | * | 12/1980 | Barnett | 126/21 R |
| 4,535,386 | A | | 8/1985 | Frey, Jr. et al. | |
| 4,858,069 | A | | 8/1989 | Hughes | |
| 4,872,102 | A | | 10/1989 | Getter | |
| 5,008,775 | A | | 4/1991 | Schindler et al. | |
| 5,255,736 | A | | 10/1993 | Kotlyar | |
| 5,258,888 | A | | 11/1993 | Korinsky | |

(Continued)

FOREIGN PATENT DOCUMENTS

WO 2008056993 A2 5/2008

OTHER PUBLICATIONS

Partial European Search Report received in counterpart European Application No. EP 08167310.5-2320 (6 pages).

(Continued)

*Primary Examiner* — Sang Paik
(74) *Attorney, Agent, or Firm* — Wood, Herron & Evans, LLP

(57) ABSTRACT

A heater unit for a respiratory system is designed for natural convection cooling air to pass first through a transformer in the heater unit and then through a heat sink in the heater unit to which is mounted a power switch to conduct heat from the power switch to the cooling air passing through the heat sink. A thermal break may be provided between the heat sink and the transformer. The transformer may be a toroidal transformer with the air passing through an aperture thereof such as from a hollow projection of the heater unit extending into the aperture. One side of the transformer may be situated along a surface of the heater unit and the heat sink secured to the heater unit against the opposite side of the transformer to hold the transformer in place. A venting chamber may be associated with an air exhaust of the heater unit to provide a circuitous exit path for air exiting the heater unit. The venting chamber may extend in generally surrounding relationship with the heater of the heater unit.

34 Claims, 7 Drawing Sheets

U.S. PATENT DOCUMENTS

| | | | |
|---|---|---|---|
| 5,285,350 A | | 2/1994 | Villaume |
| 5,446,268 A | * | 8/1995 | Chen .......................... 219/623 |
| 5,487,380 A | | 1/1996 | Grabenkort |
| 5,513,071 A | | 4/1996 | LaViolette et al. |
| 5,596,483 A | | 1/1997 | Wyler |
| 5,632,918 A | | 5/1997 | Zook et al. |
| 5,717,189 A | * | 2/1998 | Goetz et al. .................. 219/483 |
| 5,781,411 A | | 7/1998 | Feenstra |
| 5,784,255 A | | 7/1998 | Wyland |
| 5,829,515 A | | 11/1998 | Jeffries et al. |
| 5,894,407 A | | 4/1999 | Aakalu et al. |
| 5,912,800 A | | 6/1999 | Sammakia et al. |
| 5,912,803 A | | 6/1999 | Dahl et al. |
| 5,943,473 A | | 8/1999 | Levine |
| 6,034,873 A | | 3/2000 | Stahl et al. |
| 6,046,906 A | | 4/2000 | Tseng |
| 6,054,198 A | * | 4/2000 | Bunyan et al. .............. 428/40.5 |
| 6,084,770 A | | 7/2000 | Wyland |
| 6,088,225 A | | 7/2000 | Parry et al. |
| 6,118,656 A | | 9/2000 | Wang |
| 6,132,310 A | | 10/2000 | Baribeault et al. |
| 6,175,494 B1 | | 1/2001 | Komatsu |
| 6,324,056 B1 | | 11/2001 | Breier et al. |
| 6,339,212 B1 | | 1/2002 | Campbell |
| 6,404,634 B1 | | 6/2002 | Mann |
| 6,459,577 B1 | | 10/2002 | Holmes et al. |
| 6,477,053 B1 | | 11/2002 | Zeidan et al. |
| 6,504,719 B2 | | 1/2003 | Konstad et al. |
| 6,518,868 B1 | | 2/2003 | Miller et al. |
| 6,563,410 B1 | | 5/2003 | Marton |
| 6,580,608 B1 | | 6/2003 | Searls et al. |
| 6,691,769 B2 | | 2/2004 | Johnson et al. |
| 6,707,676 B1 | | 3/2004 | Geva et al. |
| 6,961,241 B2 | | 11/2005 | Lee |
| 6,988,497 B2 | | 1/2006 | Levine |
| 7,714,686 B2 | * | 5/2010 | Meyer et al. .................. 336/61 |
| 7,732,740 B2 | * | 6/2010 | Hsien Shan ............. 219/452.11 |
| 2001/0032718 A1 | | 10/2001 | Sheerin et al. |
| 2003/0062149 A1 | | 4/2003 | Goodson et al. |
| 2003/0128971 A1 | | 7/2003 | Birdsell et al. |
| 2003/0174037 A1 | | 9/2003 | Hooey et al. |
| 2003/0206400 A1 | | 11/2003 | Heirich et al. |
| 2004/0114330 A1 | | 6/2004 | Yazawa |
| 2005/0219814 A1 | | 10/2005 | Yazawa |
| 2005/0265702 A1 | | 12/2005 | Birdsell et al. |
| 2007/0101999 A1 | | 5/2007 | Duquette et al. |
| 2008/0054497 A1 | | 3/2008 | Bradley et al. |
| 2008/0054500 A1 | | 3/2008 | Bradley et al. |

OTHER PUBLICATIONS

Official Action issued in counterpart European Application No. 08 167 310.5 dated Feb. 18, 2010 (4 pages).
Manual for Fisher & Paykel Model Nos. MR700, MR720, MR730 Respiratory Humidifiers (Mar. 1998) (48 pages).
Technical Manual Fisher & Paykel Respiratory Humidifier Model Nos. MR700, MR720, MR730, Mr 480 (Mar. 2001) (64 pages).
Allegiance Healthcare 510K No. K993833 for Airlife® Heated Ventilator and Anesthesia Breathing Circuits (5 pages) (Dec. 10, 1999).
Brochure for Hudson RCI Humid-Heat® (6 pages).
Operating Manual for Fisher & Paykel Model Nos. MR700, MR720, MR730 Respiratory Humidifiers (Mar. 1994) (46 pages).
Instruction Sheet for Airlife® Single Heated Adult Respiratory Circuit (2 pages) (date uncertain).
Cardinal Health RT110 Data for Circuits, reprinted from the internet Jun. 3, 2006 (2 pages).
Fisher & Paykel 900MR561 Temperature Probe Label (one page) (date uncertain).
Fisher & Paykel Airway Temperature Probes Instructions for Use (3 pages) (2003).
Cat. RT110 Insert for Airlife™ Adult Respiratory Circuit—Heated (one page) (undated).

* cited by examiner

RESPIRATORY SYSTEM HEATER UNIT

FIELD OF THE INVENTION

The present invention relates generally to respiratory systems, and more particularly, to a heater unit of such a system.

BACKGROUND

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit. An expiratory limb hose or conduit may be provided to allow air to expel from the patient.

It is typically desired to warm and impart humidity to the breathable gas before it is provided to the patient. For that purpose, many respiratory systems include a heater system having a chamber for holding water and a heater unit supporting a heater, which may be comprised of one or more heating elements and a metal plate defining a hot plate. A wall of the chamber, such as the bottom surface of the chamber, is thermally conductive. The chamber is removably supported on the heater unit with the bottom surface in thermal contact with the hot plate of the heater to thus heat the water in the chamber. The chamber may be manually refillable, or there may be a water source to selectively fill the chamber as it empties. The breathable gas is coupled to the chamber and is passed through the chamber to be heated and humidified. An example of a heater and chamber arrangement is shown in U.S. Pat. Nos. 6,988,497 and 5,943,473. The inspiratory limb carries the heated and humidified gas to the patient. The inspiratory and/or expiratory limbs may also be heated such as by heater circuits comprised of heater wires running through and along the hose or conduit interior.

The heater unit typically also houses several other heat generating components, such as an electrical transformer, controller circuitry, and power switches (which may be thermally coupled to a heat sink), utilized to regulate the temperature of the heater and provide power to regulate heat input to the limbs from the heater circuits thereof. These components are disposed within the heater unit and consequently heat the air therein which then needs to be cleared from the heater unit to avoid overheating. Otherwise, the performance and life expectancy of the heater unit may be adversely affected. It is known to provide a fan within a housing to force air through the housing in order to cool the air and/or components therein. Fans are not desired for heater units of a respiratory system, which instead rely principally on flow of air therethrough from natural convection cooling. By way of example, a heater unit may have one or more air inlets adjacent to or contained within the bottom of the heater unit, and one or more air exhausts adjacent to or contained within the top of the heater unit, such that as the heated air therein naturally rises, cooler air will be brought in through the air inlets and the hotter air will exit from the air exhausts.

Use of natural convection cooling is thus helpful to remove heated air, but there are some disadvantages with prior designs. Further, evolving design requirements for heater units used in respiratory systems impose increased control functionality requirements and more stringent response times, all of which create additional heating load within the heater unit. But hospital and other constraints may limit the general size of the heater unit, such that there could be insufficient cooling.

SUMMARY OF THE INVENTION

The present invention provides a heater unit design with sufficient cooling while overcoming disadvantages of prior designs. To that end, and in accordance with one aspect of the present invention, a heater unit for a respiratory system is provided in which the transformer and the heat sink thermally coupled to the power switches are positioned such that natural convection cooling carries air first through the transformer and then through the heat sink which facilitates effective cooling of the transformer and power switches. The arrangement of the present invention has the further advantage that heat transfer from the heat sink and power switches to the transformer is minimized. Heat transfer to the transformer is further minimized by inclusion of a thermal break between the transformer and the heat sink.

In one embodiment, the electrical transformer may be a toroidal transformer defining an aperture therethrough. The air flow path is created through that aperture. In that regard, one or more of the air inlets may be defined on a hollow projection from the bottom of the heater unit. The toroidal transformer may be located over that projection, such as with the projection extending partially into the transformer aperture. Cooler outside air is thus available within the transformer aperture to form the air path therethrough.

In accordance with another aspect of the present invention, the heat sink may be used not only for heat transfer, but also to hold the electrical transformer in place within the heater unit. To that end, one side of the transformer may be situated along a surface of the heater unit, with the heat sink secured to the heater unit against the opposite side of the transformer. In the embodiment where the transformer is a toroidal transformer situated over the hollow projection, the heat sink may be secured to the heater unit above, and in the air flow path of, the hollow projection. To help minimize heat transfer from the heat sink to the transformer, a thermal break may be provided therebetween in the form of an elastomeric member, which may be shaped like a disk having an aperture for the air flow path to extend therethrough.

In accordance with a yet further aspect of the present invention, the heater unit includes a venting chamber into which the heated air exits from the air exhaust(s). The chamber provides a circuitous exit path for the heated air so as to generally block inadvertent liquid access to the air exhausts while still allowing heated air to exit the heater unit. In that way, the heater unit can be cleaned without leaving the internal components at risk from damage to cleaning or other fluid easily passing into the heater unit through the air exhausts, as was possible in a prior heater unit. The vent chamber may extend in generally surrounding relationship with the hot plate of the heater such that the circuitous exit path is also in generally surrounding relationship with the hot plate. That relationship surprisingly enhances the natural convection cooling within the heater unit when the hot plate is heated up.

By virtue of the foregoing, there is thus provided a heater unit design with sufficient cooling while overcoming disadvantages of prior designs. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF THE DRAWINGS

Figure 1:
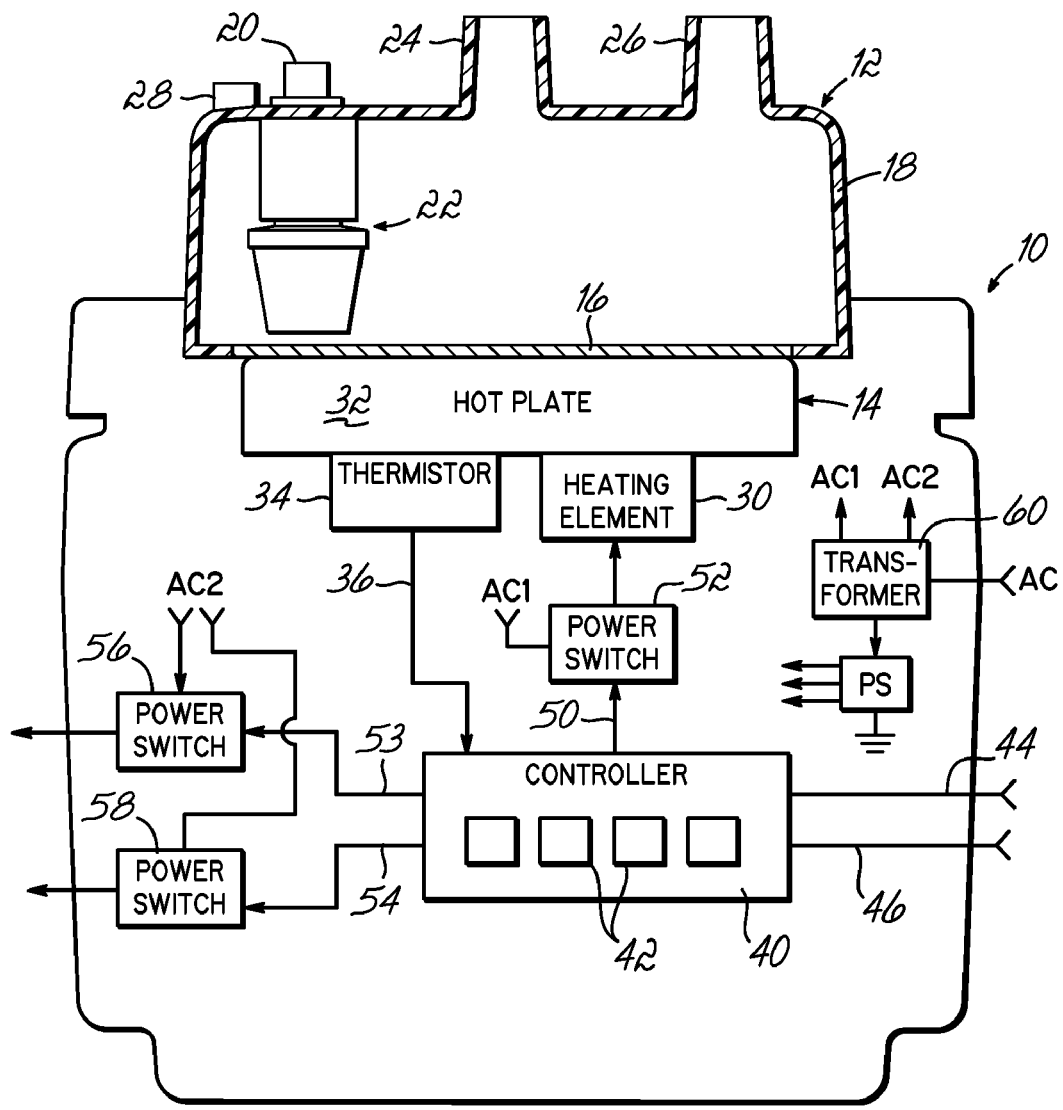
FIG. 1 is a diagram of a heater unit designed in accordance with the principles of the present invention and a chamber for use in a respiratory system.
Figure 2:
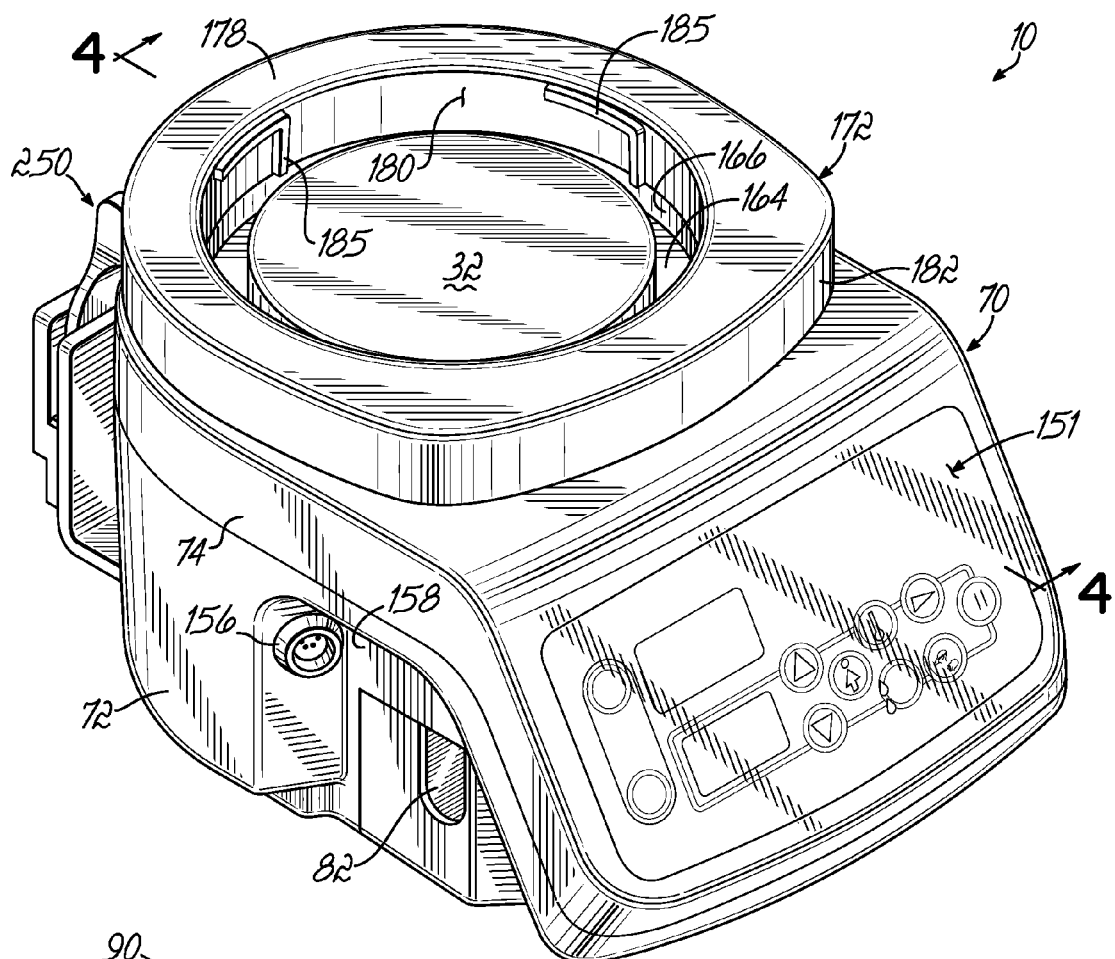
FIG. 2 is an isometric view of an embodiment of the heater unit shown in FIG. 1.

FIG. 1 is a diagrammatic view of a heater unit 10 designed in accordance with the principles of the present invention, in combination with a heatable container such as a disposable chamber 12 adapted to hold water (not shown) and to be heated through a heater 14 of heater unit 10. To that end, chamber 12 includes a metal bottom wall 16 adapted to be in thermal communication with heater 14, and a plastic housing 18 fitted to wall 16 and adapted to hold water therein as obtained from a water supply (not shown) fluidicly coupled through water inlet 20 as regulated by float valve assembly 22. Housing 18 also includes gas ports 24, 26 for the flow of gas into and out of chamber 12 in order to heat and humidify the gas flowing therethrough. Chamber 12 may also include a vent 28 for purposes of venting the water supply (not shown). More details of suitable chambers, vented water supplies, and prior heaters for heating chamber 12 are shown in U.S. Pat. Nos. 6,988,497 and 5,943,473, and co-pending U.S. patent application Ser. Nos. 11/469,086 filed Aug. 31, 2006 and Ser. No. 11/469,113 filed Aug. 31, 2006, the disclosures of all four of which are incorporated herein by reference in their entireties.

Heater 14 of heater unit 10 may include one or more electrically energizable heater elements 30 thermally coupled to a hot plate 32 for heating thereof. Hot plate 32 is adapted to be placed into confronting and thermally conductive relationship with bottom wall 16 of chamber 12. Details of a suitable heater 14 are described in concurrently-filed U.S. patent application Ser. No. 11/926,982 the disclosure of which is incorporated herein by reference in its entirety. Thermally coupled to hot plate 32 is a temperature responsive device 34, such as thermistor to provide signals as at 36 corresponding to the temperature of hot plate 32. Heater unit 10 also includes a controller 40 which may include various electronic components 42 adapted to obtain signals 36, as well as signals as at 44 and 46 related to temperature measurements obtained from a breathing circuit (not shown). Controller 40 is adapted to utilize signals 36, 44 and/or 46 to generate a first power signal as at 50 by which to selectively electrically energize a power switch 52 which, in turn, selectively energizes heater element(s) 30 so as to regulate the temperature of hot plate 32 as desired. Controller 40 is also adapted to output inspiratory and expiratory power signals as at 53, 54, respectively, to selectively electrically energize respective power switches 56 and 58. Power switches 56 and 58 are adapted to be coupled to respective heating circuits (not shown) of the inspiratory and expiratory limbs of a breathing circuit (also not shown). Controller 40 and its function, in relation to power switches 52, 56 and/or 58, may be as set out in greater detail in the following concurrently-filed patent applications: U.S. patent application Ser. No. 11/927,013; U.S. patent application Ser. No. 11/926,990; U.S. patent application Ser. No. 11/927,000; U.S. patent application Ser. No. 11/927,004; U.S. patent application Ser. No. 11/927,054; and U.S. patent application Ser. No. 11/927,068; the disclosures of all six of which are incorporated herein by reference in their entireties.

Power Switches 52, 56 and 58, which may be triacs or other electronic switching devices, are significant sources of heat within heater unit 10. Additionally, an electric transformer 60 is included within heater unit 10 to provide various levels of AC power (such as via one or more taps AC1 and AC2 thereof) to power heater 14 through power switch 52, as well as the heating circuits of a breathing circuit (both not shown) through power switches 56 and 58. Transformer 60 is a further significant source of heat within heater unit 10. Electronic components 42 of controller 40 may also be sources of heating within heater unit 10 (power switches 52, 56 and/or 58 may also be considered to be part of controller 40, although they could also be separate therefrom). Heater unit 10 is designed to provide airflow therethrough sufficient to avoid overheating the various components within heater unit 10, as will now be described by reference to one embodiment thereof shown in FIGS. 2 through 8.

Figure 3:
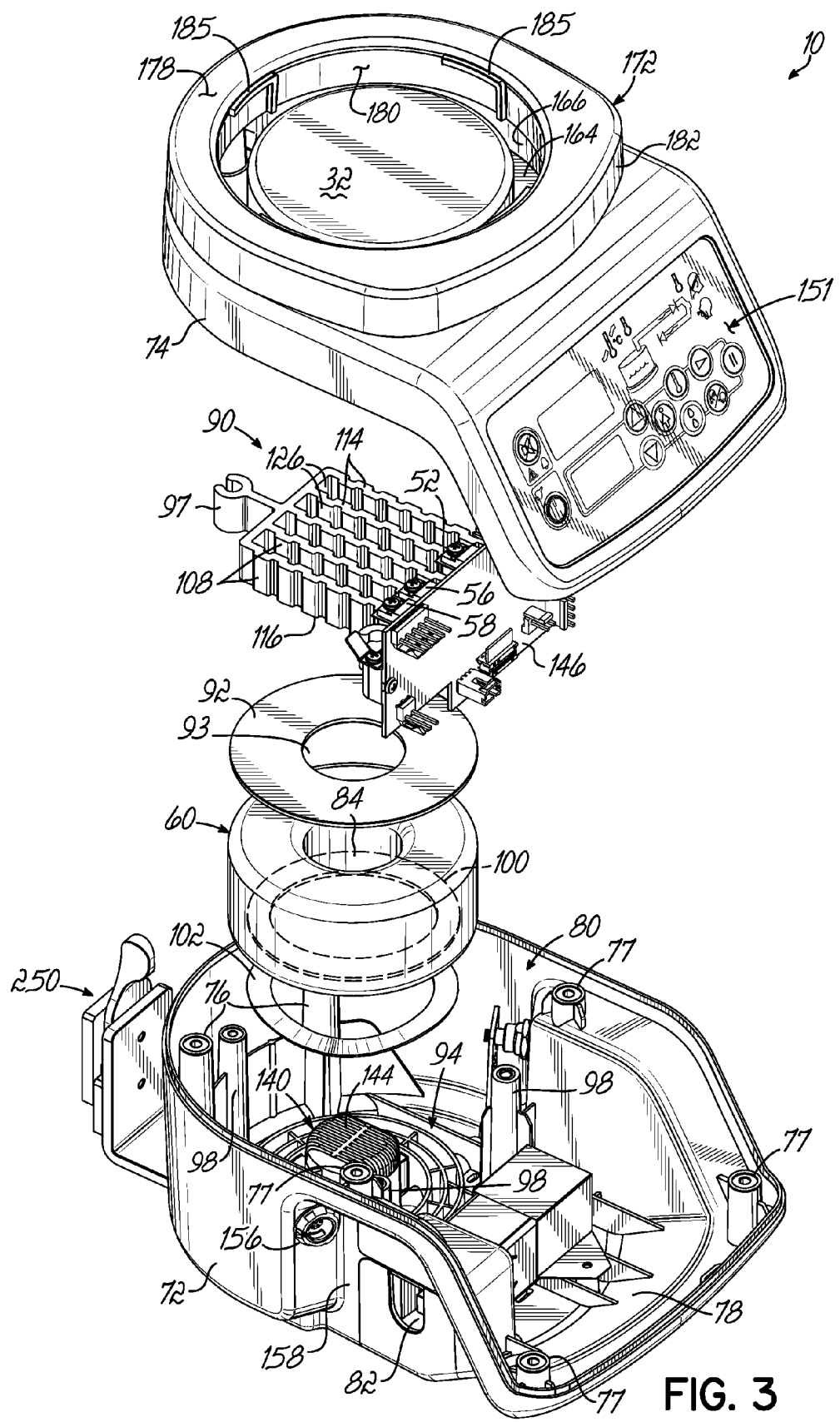
FIG. 3 is an exploded, isometric assembly view of the heater unit of FIG. 2.
Figure 4:
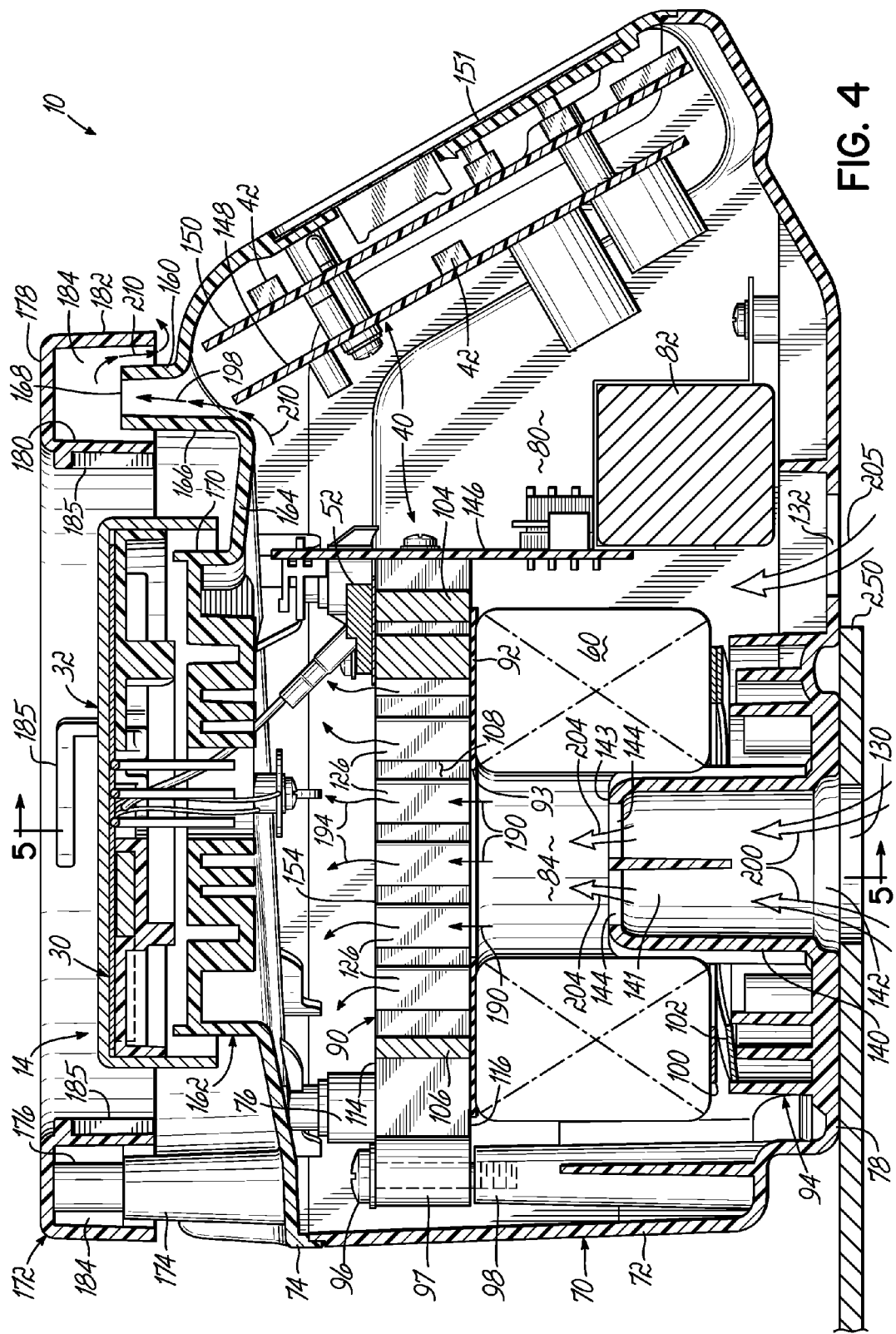
FIG. 4 is a cross-sectional view taken along line 4-4 in FIG. 2.
Figure 5:
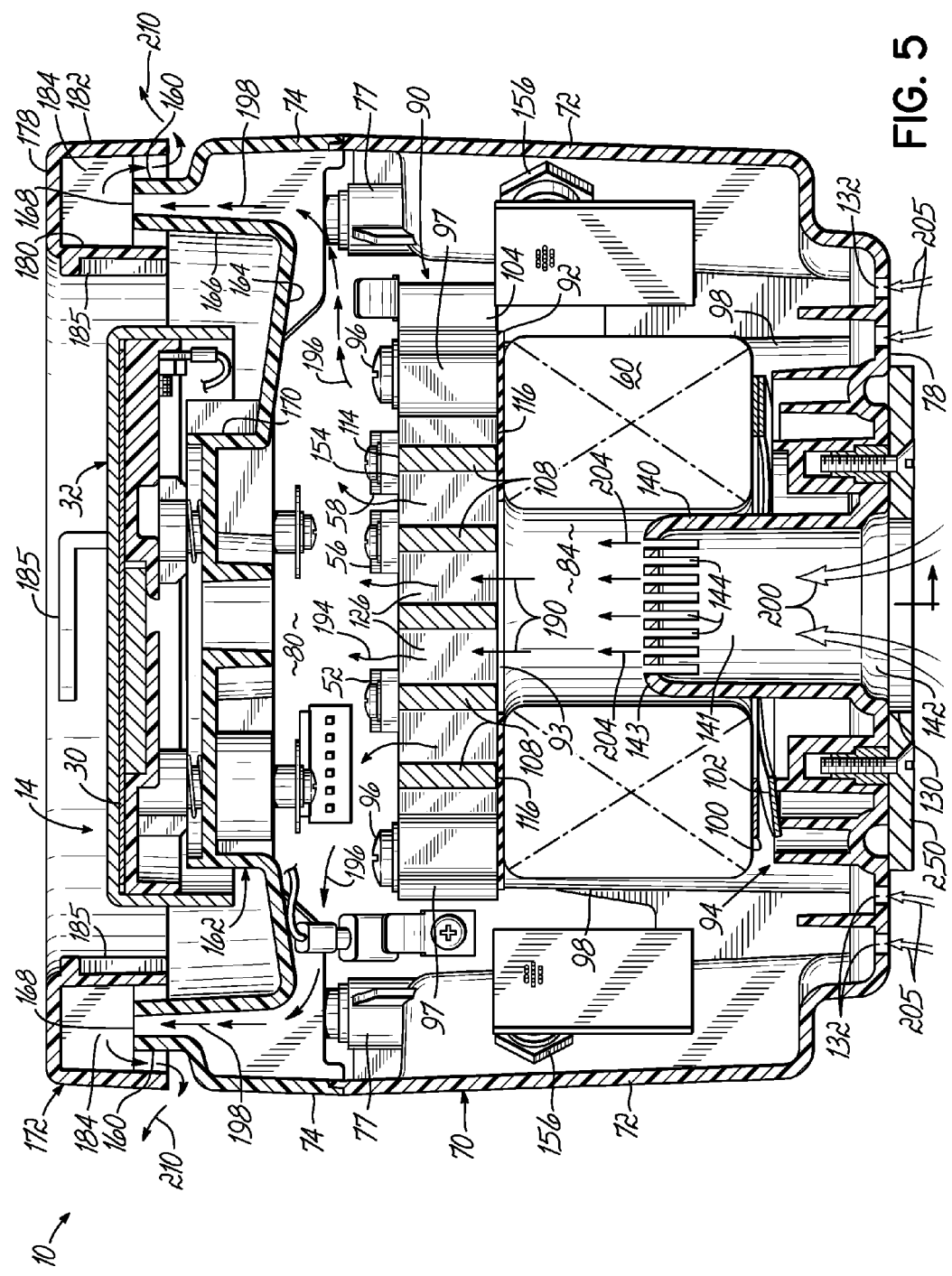
FIG. 5 is a cross-sectional view taken along line 5-5 in FIG. 4.
Figure 7:
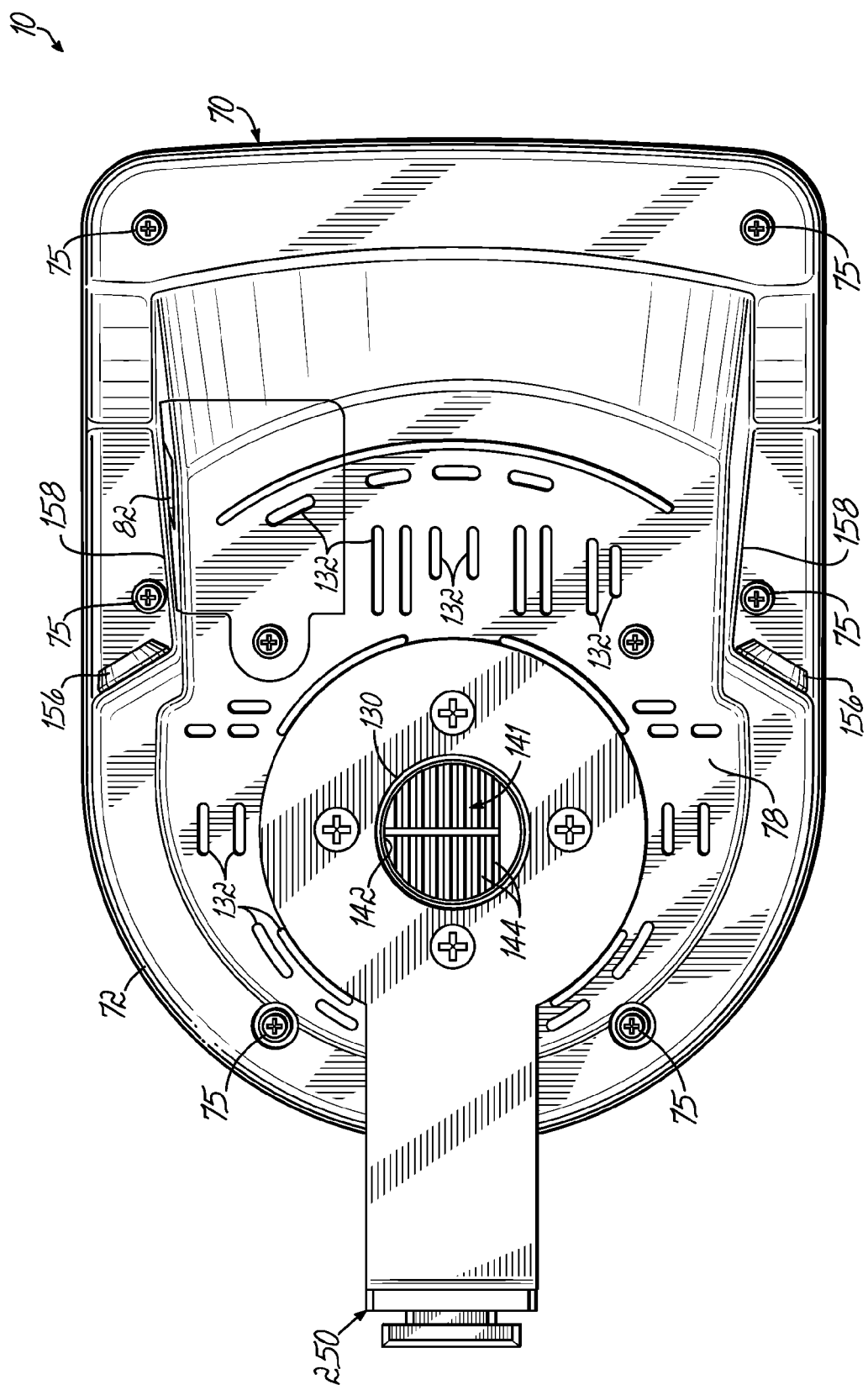
FIG. 7 is a bottom plan view of the heater unit of FIG. 2.

Heater unit 10 is defined by a housing 70 having a lower housing shell 72 and an upper housing shell 74 secured together with conventional fasteners, such as screws 75 (FIG. 7) which pass through a pair of posts 76 and two pairs of bosses 77 (FIG. 3). Posts 76 and bosses 77 extend upwardly from a base 78 of lower housing shell 72 into mating bosses (not shown) of upper housing shell 74. Lower and upper housing shells 72, 74 to define an interior chamber 80 of housing 70 (FIGS. 4 and 5).

Electric transformer 60 is disposed within the interior chamber 80 and couples via junction box 82 to a source of AC (not shown). Transformer 60 is adapted to provide various levels of AC output power via taps thereof (not shown) for use by controller 40 and power switches 52, 56 and 58. A power supply (PS) may also obtain AC power from transformer 60, or junction box 82, to also provide various levels of DC voltages for use by components 42 of controller 40 as will be readily understood. Transformer 60 is a toroidal transformer defining an interior aperture 84 therethrough. An extruded aluminum heat sink 90 is disposed within interior chamber 80 above transformer 60. An elastomeric member, such as a relatively thin, washer-like disk 92 (FIG. 3), is disposed to be sandwiched between the top side of transformer 60 and heat sink 90. Disk 92 has a diameter about equal to that of transformer 60 and includes an aperture 93 sized to match transformer aperture 84. Disk 92 may be made of an elastomeric material to serve as a mechanical damper, an electrical insulator and/or a thermal break. Transformer 60 is advantageously held in place within housing 70 clamped between heat sink 90 and a support structure 94 that extends upwardly from base 78 of lower housing shell 72 to define an interior surface within interior chamber 80. To that end, conventional fasteners, such as screws 96 (FIGS. 4 and 5) extend through bosses 97 of heat sink 90 into mating posts 98 extending upwardly from base 78 of lower housing shell 72. To improve structural integrity, in addition to disk 92, a washer 100 and a resilient member 102, such as a Belleville washer, may be disposed between transformer 60 and support structure 94. Resilient member 102, alone or in cooperation with washer 100, provides a cushion between the bottom side of transformer 60 and the adjacent surface defined by support structure 94.

Figure 6:
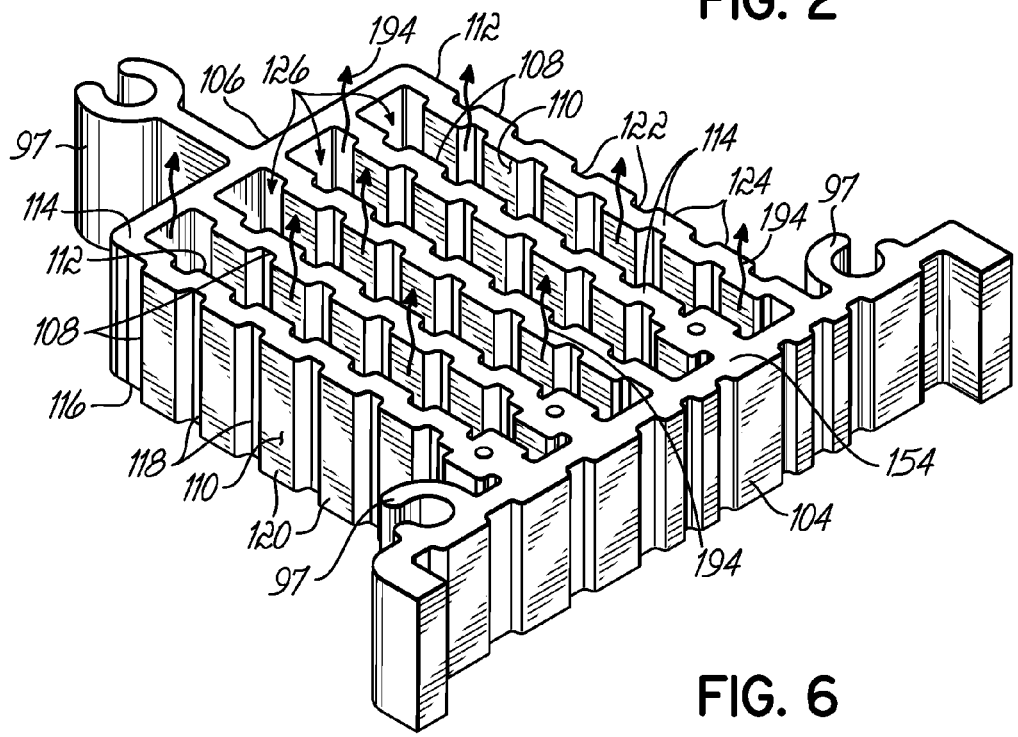
FIG. 6 is an isometric view of the heat sink incorporated in the heater unit of FIG. 2.

With specific reference to FIG. 6, heat sink 90 includes opposing first and second walls 104 and 106 and a plurality of fins 108 that are spaced apart from one another and extend between walls 104 and 106. Each of fins 108 has a first side surface 110, a second side surface 112, an upper surface 114 and a lower surface 116. Fins 108 may have a generally corrugated shape defined by a plurality of alternating grooves 118 and columns 120 of first side surface 110 and a plurality of alternating grooves 122 and columns 124 of second side surface 112. Wall 104 may also include a plurality of alternating grooves and columns (not numbered). Fins 108 cooperate to define a plurality of air flow channels 126 passing through heat sink 90 between walls 104 and 106.

Housing 70 includes a first air inlet 130 in lower housing shell 72 and extending through base 78 thereof. Base 78 may also include a plurality of apertures 132 disposed outwardly of air inlet 130 to define further air inlets of various size, shape and orientation. A hollow projection 140 extends upwardly from base 78 sized to receive toroidal transformer 60 thereover and into aperture 84 thereof so as to position transformer 60 within housing 70. Projection 140 defines an inner passage 141 open at a lower end 142 to couple with or define air inlet 130. The upper end 143 of projection 140 includes a plurality of apertures 144 formed therein and through which air from first air inlet 130 may communicate into aperture 84 of transformer 60 for convection cooling of transformer 60 by air passing through aperture 84 from projection 140 as will be described.

Controller 40 may be comprised of a plurality of printed circuit boards 146, 148 150 (FIG. 4) for components 42 (only one shown on each of circuit boards 148 and 150 for sake of clarity) and a user interface panel 151. Power switches 52, 56 and 58 may be mounted to circuit board 146 and secured in thermal communication with heat sink 90 such as along top 154 thereof by being mounted by fasteners to heat sink 90, by which to conduct heat from the power switches into heat sink 90 for convection cooling by air passing through air flow channels 126 as will be described. Signals 44, 46 from temperature probes (not shown) as well as power from power switches 56 and 58, are coupled into and out of heater unit 10 via respective connectors 156 located within recess 158 of lower housing shell 72 of housing 70 whereby to protect and separate connectors 156 and the associated electrical connections.

Figure 8:
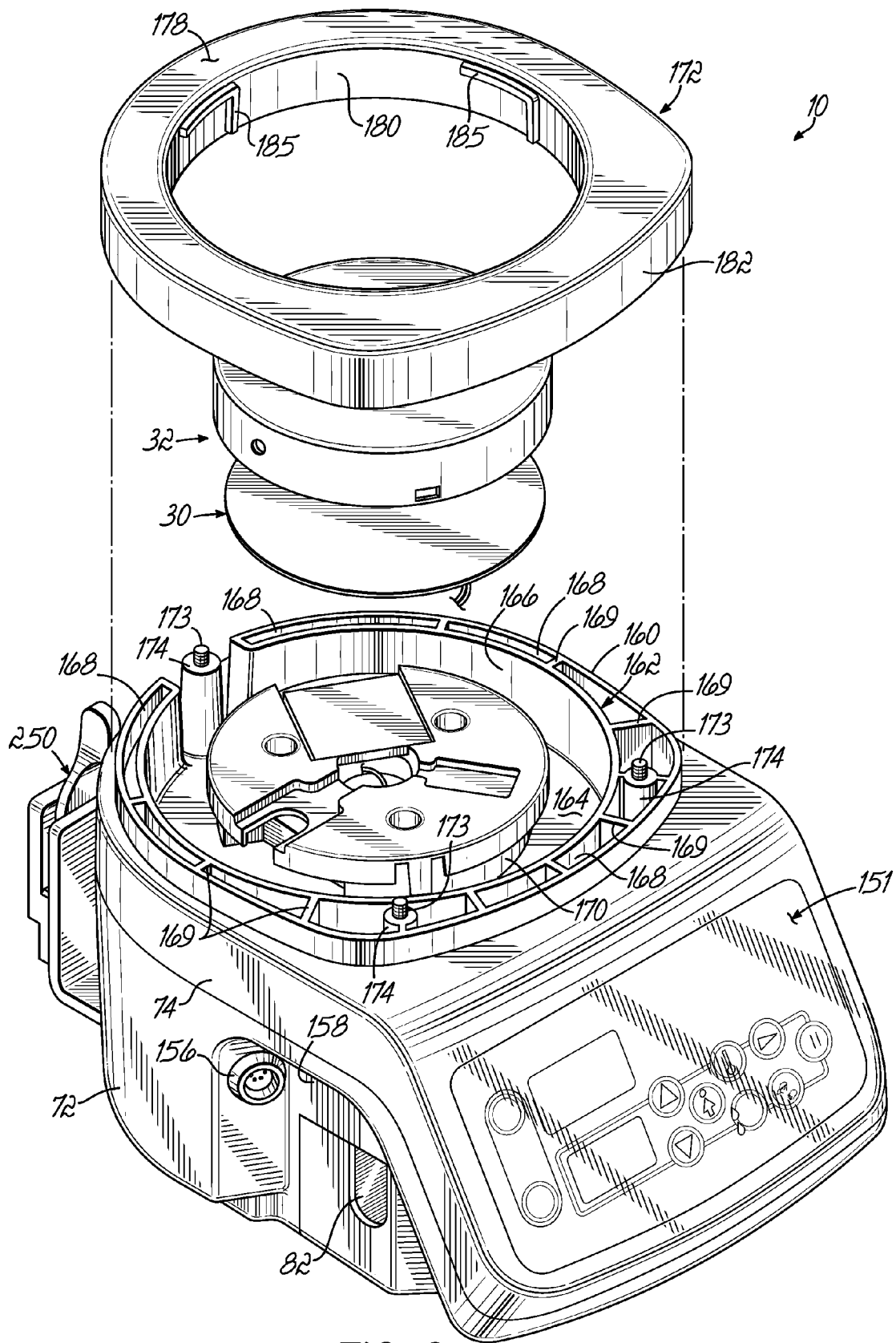
FIG. 8 is an exploded, isometric assembly view of an upper portion of the heater unit of FIG. 2.

Upper housing shell 74 includes an upper flange 160 extending about the perimeter thereof and a support structure, indicated generally at 162, defined by a base 164 and an upwardly extending flange 166 which is in generally confronting, spaced apart relationship with upper flange 160 to define an upwardly extending air exhaust 168. Flanges 160 and 166 are interconnected by a plurality of circumferentially spaced connecting struts 169 (FIG. 8). Support structure 162 also includes a platform 170 extending upwardly from base 164 to support heater 14 as explained in greater detail in aforementioned concurrently-filed U.S. patent application Ser. No. 11/926,982. Base 164 and platform 170 may provide a thermal break between heater 14 and interior chamber 80.

A locking ring 172 is mounted to heater unit 10 extending in generally surrounding relationship with hot plate 32, and in overlying relationship to air exhaust 168 for purposes to be described. Locking ring 172 is secured to upper housing shell 74 by a plurality of fasteners 173 that pass upwardly through circumferentially spaced bosses 174 (FIG. 8) and into corresponding ones of a plurality of bosses 176 (only one shown in FIG. 4) formed in locking ring 172, that extend downwardly from an upper member or roof 178 of locking ring 172. Locking ring 172 further includes an inner flange 180 and an outer flange 182 connected by the upper member 178 so as to define an inverted U-shape cross-section of locking ring 172 forming a downwardly facing chamber 184 (i.e., chamber 184 is open at the bottom and closed at the top) extending about the perimeter of locking ring 172. Locking ring includes locking tabs 185 on inner flange 180 by which to selectively secure chamber 12 to heater unit 10 with its wall 16 confronting and in thermal communication with hot plate 32 for heating of water in chamber 12. The arrangement and shape of locking ring 172 serves to define a circuitous exit path between exhaust outlet 168 and the environment through chamber 184. One advantage of that circuitous exit path is to minimize the risk that cleaning or other fluids could easily pass into interior chamber 80 of housing 70 and damage the components therein.

When transformer 60 is operating, it will generate heat within interior chamber 80. Similarly, when power switches 52, 56 and/or 58 are operating, they will generate heat within interior chamber 80, but that heat will be largely conducted through heat sink to air flow channels 126. As particularly seen in FIGS. 4 and 5, the arrangement of transformer 60 and heat sink 90 serve to create a natural convection air path between air inlet 130 and air exhaust 168, which causes air to be carried first through transformer 60 and then through heat sink 90 to thereby facilitate effective cooling of transformer 60 and power switches 52, 56 and 58. To that end, the alignment of upper end 143 of hollow projection 140, aperture 84 of transformer 60 and air flow channels 126 of heat sink 90 induces hot air to rise upward along the air path as exemplified by arrows 190 so as to flow through heat sink air flow channels 126 and over power switches 52, 56 and 58, and towards air exhaust 168 as exemplified by arrows 194, 196 and 198. That, in turn, causes air to be drawn into interior chamber 80, and particularly through hollow projection 140 so as to enter within aperture 84 of transformer 60 as exemplified by arrows 200 and 204.

As thus described, natural convection sets up the desired air path for effective cooling of transformer 60 and power switches 52, 56 and 58. Additional air flow is induced into air inlets 132 as exemplified by arrows 205, and combines with other air flowing through interior chamber 80 to air exhaust 168 to thus further cool interior chamber 80 which in turn helps to further cool transformer 60 and power switches 52, 56 and 58, as well as other heat generating circuitry within or thermally communicating with interior chamber 80, such as components 42 by way of example. The foregoing arrangement has the further advantage that an air path for cooling passes first through transformer 60 (arrows 200 and 190) and then through heat sink 90 (arrows 190 and 194) to create an effective flow of cooling air (i.e., hot air removal). At the same time, it is expected that power switches 52, 56 and 58 may generate more heat than transformer 60, such that it is desirable not to create a situation where heat from heat sink 90 would tend to heat up transformer 60. It is believed that the arrangement as above described helps avoid such a situation. Further, the presence of disk 92 creates a thermal break between transformer 60 and heat sink 90 to further minimize the risk of heating of transformer by heat sink 90. A thermal break could be otherwise created, such as by an air gap or other insulator, particularly where heat sink 90 is not used to secure transformer 60 in place.

As mentioned, locking ring 172 creates a circuitous exit path which, as exemplified by arrows 210, expels the hot air from air exhaust 168 along the open bottom of chamber 184 of locking ring 172 to the atmosphere outside of heater unit 10. To that end, chamber 184 of locking ring 172 thus serves as a venting chamber for air exhaust 168. With venting chamber 184 in generally surrounding relationship with hot plate 32, natural convection cooling of interior chamber 80 of housing 70 is surprisingly enhanced when hot plate 32 is heated up.

In use, heater unit 10 is operated to heat water within chamber 12 to facilitate heating and humidifying breathable gas to be provided to a patient (not shown), which results in heat being generated within housing 70 such as by operation of transformer 60 and power switch 52, if not also power switches 56 and 58 if a heated breathing circuit (not shown) is attached to heater unit 10. The design of heater unit 10 is such that natural convection cooling causes air to pass first through transformer 60 and then through heat sink 90 to facilitate effective cooling of transformer 60 and power switch 52 (and switches 56 and 58 if being operated). Heater unit 10 may be removably secured to a support structure (not shown) by a self-aligning locking mechanism 250 attached to heater unit 10 as described in concurrently-filed U.S. patent application Ser. No. 11/927,044, the disclosure of which is incorporated herein by reference in its entirety.

By virtue of the foregoing, there is thus provided a heater unit design with sufficient cooling while overcoming disadvantages of prior designs.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. By way of example, while a low thermal mass hot plate 32 is shown, a thicker plate and/or a higher thermal mass metal or other member could be provided for hot plate 32. Further, a plurality of air exhausts could be provided. In that same regard, while air exhaust 168 is considered to be one air exhaust, due to struts 169, it is seen that air exhaust may be comprised of a plurality of segments each of which could be considered an air exhaust. Still further, if desired, a fan (not shown) could be added, such as within hollow projection 140 or elsewhere, to provide or enhance the flow of air through interior chamber 80 and/or through transformer 60 and heat sink 90. The invention in its broader aspects is, therefore, not limited to the specific details, representative apparatus and method, and illustrative examples shown and described. Accordingly, departures may be made from such details without departing from the spirit and scope of the general inventive concept.

Having described the invention, what is claimed is:

1. A heater unit adapted to be used with a water container in a respiratory system and configured to be cooled by natural convection, the heater unit comprising:
a housing having an air inlet adjacent a bottom thereof and an air exhaust adjacent a top thereof and defining an interior chamber therebetween;
a heated hot plate supported adjacent the top of the housing;
locking structure on the housing adapted to selectively secure a water container to the housing in thermal communication with the hot plate;
an electrical transformer and a power switch within the interior chamber of the housing;
a heat sink within the interior chamber of the housing and in thermal communication with the power switch;
the transformer and the heat sink being positioned such that a natural convection air path carries air from the air inlet, upwardly through the transformer, upwardly through the heat sink, and out the air exhaust.

2. The heater unit of claim 1, the transformer being a toroidal transformer and being positioned such that said natural convection air path extends through an aperture of the toroidal transformer.

3. The heater unit of claim 2 further comprising a hollow projection extending from the air inlet into the aperture of the toroidal transformer.

4. The heater unit of claim 3, the heat sink being secured to the heater unit above the toroidal transformer.

5. The heater unit of claim 1, one side of the transformer being situated against a surface of the housing and the heat sink being secured to the housing against an opposite side of the transformer.

6. The heater unit of claim 1, the heat sink including a plurality of fins defining air flow channels through the heat sink.

7. The heater unit of claim 1 further comprising a venting chamber associated with the air exhaust.

8. The heater unit of claim 7, the venting chamber and air exhaust cooperating to define a circuitous exit path for air exiting the air exhaust.

9. The heater unit of claim 8, the venting chamber extending in generally surrounding relationship with the hot plate.

10. The heater unit of claim 8, the air exhaust extending into the venting chamber.

11. The heater unit of claim 8 wherein the venting chamber and the air exhaust are configured such that the circuitous exit path carries air upwardly, then radially outwardly, then downwardly, then radially outwardly, then upwardly.

12. The heater unit of claim 7, the venting chamber extending in generally surrounding relationship with the hot plate.

13. A heater unit adapted to be used with a water container in a respiratory system and configured to be cooled by natural convection, the heater unit comprising:
a housing defining an interior chamber;
a heated hot plate supported by the housing;
locking structure on the housing adapted to selectively secure a water container to the housing in thermal communication with the hot plate;
an electrical transformer and a power switch within the interior chamber of the housing;
a heat sink within the interior chamber of the housing and in thermal communication with the power switch;
a first side of the transformer being situated against a surface of the housing and the heat sink being secured to the housing against a second, opposite side of the transformer.

14. The heater unit of claim 13 further comprising an elastomeric member sandwiched between the second, opposite side of the transformer and the heat sink.

15. The heater unit of claim 13 further comprising a cushion sandwiched between the first side of the transformer and the surface of the housing.

16. The heater unit of claim 13 the transformer being a toroidal transformer, the heater unit further comprising a hollow projection over which the toroidal transformer is situated with the hollow projection extending an aperture of the toroidal transformer.

17. A heater unit adapted to be used with a water container in a respiratory system and configured to be cooled by natural convection, the heater unit comprising:
a housing having an air inlet and an air exhaust and defining an interior chamber therebetween;
a heated hot plate supported adjacent the air exhaust;

locking structure on the housing adapted to selectively secure a water container to the housing in thermal communication with the hot plate;

heat generating electrical components within the interior chamber of the housing adapted to be cooled by air passing into the air inlet, upwardly through the interior chamber, and out the air exhaust; and a venting chamber associated with the air exhaust.

18. The heater unit of claim 17, the venting chamber and the air exhaust cooperating to define a circuitous exit path for air passing out the air exhaust.

19. The heater unit of claim 18, the venting chamber extending in generally surrounding relationship with the hot plate.

20. The heater unit of claim 18 the air exhaust extending into the venting chamber.

21. The heater unit of claim 18 wherein the venting chamber and the air exhaust are configured such that the circuitous exit path passes air upwardly, then radially outwardly, then downwardly, then radially outwardly, then upwardly.

22. The heater unit of claim 17, the venting chamber extending in generally surrounding relationship with the hot plate.

23. A method for cooling a heater unit by natural convection, the heater unit adapted to be used with a water container in a respiratory system and having an electrical transformer and a power switch within a housing defining an interior chamber of the heater unit and a heat sink within the interior chamber and in thermal communication with the power switch, the heater unit further including a heater supported by the housing and locking structure on the housing adapted to selectively secure a water container to the housing in thermal communication with the heater, the method comprising passing air upwardly through the transformer and then upwardly through the heat sink.

24. The method of claim 23 wherein the transformer is a toroidal transformer, passing air through the transformer including passing air through an aperture of the toroidal transformer.

25. The method of claim 23 wherein the heat sink includes a plurality of fins defining air flow channels through the heat sink, passing air through the heat sink including passing air through the air flow channels.

26. The method of claim 23 further comprising passing air out of the interior chamber through an air exhaust and then along a circuitous exit path.

27. The method of claim 26 wherein the step of passing air out of the interior chamber through the air exhaust and then along the circuitous exit path comprises passing air upwardly, then radially outwardly, then downwardly, then radially outwardly, then upwardly.

28. The method of claim 26 wherein the circuitous exit path extends in generally surrounding relationship with the heater of the heater unit.

29. A method of mounting an electrical transformer within a heater unit, the heater unit adapted to be used with a water container in a respiratory system, the heater unit including a housing, a heater supported by the housing, and locking structure on the housing adapted to selectively secure a water container to the housing in thermal communication with the heater, the heater unit configured to be cooled by natural convection, the method comprising positioning a first side of the transformer adjacent an interior surface of the heater unit and securing a heat sink to the heater unit against a second, opposite side of the transformer.

30. The method of claim 29 further comprising sandwiching an elastomeric member between the second side of the transformer and the heat sink.

31. The method of claim 29 further comprising sandwiching a cushion between the first side of the transformer and the interior surface of the heater unit.

32. A method of venting a heater unit by natural convection, the heater unit adapted to be used with a water container in a respiratory system, the heater unit having a housing defining an interior chamber, a heater supported by the housing, locking structure on the housing adapted to selectively secure a water container to the housing in thermal communication with the heater, and an air exhaust, the method comprising passing air upwardly and out of the interior chamber through the air exhaust and then along a circuitous exit path.

33. The method of claim 32 wherein the circuitous exit path extends in generally surrounding relationship with the heater of the heater unit.

34. The method of claim 32 wherein the step of passing air through the air exhaust and then along the circuitous exit path comprises passing air upwardly, then radially outwardly, then downwardly, then radially outwardly, then upwardly.

* * * * *